United States Patent [19]

Kappas et al.

[11] Patent Number: 5,223,494
[45] Date of Patent: Jun. 29, 1993

[54] ORALLY ADMINISTERED PORPHYRINS TO CONTROL INTESTINAL IRON ABSORPTION

[75] Inventors: Attallah Kappas; Daniel W. Rosenberg; George S. Drummond, all of New York, N.Y.

[73] Assignee: The Rockefeller University, New York, N.Y.

[21] Appl. No.: 585,232

[22] Filed: Sep. 21, 1990

Related U.S. Application Data

[63] Continuation-in-part of Ser. No. 411,842, Sep. 25, 1989, abandoned.

[51] Int. Cl.$^5$ .............................................. A61K 31/40
[52] U.S. Cl. ..................................... 514/185; 514/410
[58] Field of Search .................................. 514/185, 410

[56] References Cited

U.S. PATENT DOCUMENTS 4,996,200  2/1991  Nishimura et al. .................. 514/185

OTHER PUBLICATIONS

US, A, 4,692,440 (Kappas et al.) Sep. 8, 1987 column 5, lines 47 to 61, and column 6, lines 1 to 27.
US, A, 4,684,637 (Kappas et al.) Aug. 4, 1987 column 3, lines 34 to 68 and column 6, lines 1 to 28.
US, A, 4,619,923 (Kappas et al.) Oct. 28, 1986 (Entire Document).
US, A, 4,657,902 (Kappas et al.) Apr. 14, 1987 (Entire Document).
Anderson, et al., Clinical Pharmalcology and Therapeutics, vol. 39 (5) pp. 510–520, 1986.
Maines, et al., Proc. Nat. Acad. of Science, vol. 71 (11) pp. 4293–4297, 1974.
Lowry, et al., J. Biol. Chem. 193 265–275 (1951).
Atomic Spectroscopy 2(5), 1981, pp. 137–145.
Rosenberg, et al., Biochemical Pharmacology 38(7) 1155–1161, 1989.
Maines, et al., J. Biol. Chem. 250(11) 1975 pp. 4171–4177.
Slavin et al., Analytical Chemistry 53 pp. 1504–1509, 1981.
Hintz et al., Pediactric Research, 1988 pp. 50 to 53.
Raffin, et al., J. Clinical Investigation 54 1974 1344–1352.
Stohs, et al., Arch. Biochem. and Biophysics 117 105–116 (1976).
Yoshinaga, et al. J. Biol. Chem 237(22) 7778–7785, 1982.
Kappas, et al., J. Clinical Investigation 77 (2) 1986 pp. 332–339.
Chaniotakis, et al., Anal. Chem. 1989 61 566–570.

*Primary Examiner*—Robert T. Bond
*Assistant Examiner*—E. C. Ward
*Attorney, Agent, or Firm*—Wyatt, Gerber, Burke and Badie

[57] ABSTRACT

Disclosed is a pharmaceutical composition for oral administration to control heme oxygenase comprising mettaloprotoporhyrins and mettalomesoporphyrins.

9 Claims, 2 Drawing Sheets

ORALLY ADMINISTERED PORPHYRINS TO CONTROL INTESTINAL IRON ABSORPTION

RELATED APPLICATIONS

This application is a continuation-in-part application of copending and commonly owned patent application Ser. No. 411,842 filed Sep. 25, 1989, now abandoned.

BACKGROUND OF THE INVENTION

This invention relates to metalloporphyrins such as metalloprotoporphyrins and metallomesoporphyrins, to therapeutically useful oral compositions containing these compounds together with a pharmaceutically acceptable carrier, and to the use of these compounds and compositions in treating various afflictions of animals, particularly mammals, and especially humans.

Heme is a red pigment comprised of four subunits called pyrroles; these subunits are chemically joined to form a single large tetrapyrrole (porphyrin) ring structure. A metal atom is chelated at the center of this porphyrin. In higher organisms this metal is iron and the porphyrin ring structure is called protoporphyrin IX.

In mammals and other vertebrates protoporphyrin IX, hereinafter heme is enzymatically degraded to form open chain tetrapyrroles generally called bile pigments (e.g., bilirubin, biliverdin) and iron. Heme oxygenase is the rate-limiting enzyme in the catabolism of heme to bile pigments and iron. This degradation takes place in certain organs of animals. For example, in the liver with respect to the degradation of heme from hemoglobin and other heme proteins. In the digestive system, by the action of heme oxygenase in the small intestinal epithelium, heme from foodstuffs is degraded to bile pigments and iron. The iron is then absorbed by the animal. This may result in excess iron accumulation in the body which can cause deleterious and even lethal consequences.

A chronic excess of iron may derive from several sources, e.g., cooking methods (iron pots) or directly via the diet (e.g., iron-overload induced cutaneous porphyrin), from excess therapeutic administration of the metal in an attempt to vigorously treat unresponsive anemias; from hypertransfusions to which certain patients with blood disorders are subject; idiopathically from the disorders collectively known as "hemachromatosis"; from certain industrial exposures; but the most common causes of excess iron deposition in tissues, and the resultant pathologic consequences which derive thereof, are a consequence of common congenital hemolytic anemias such as sickle cell disease, the various forms of thalassemia, G-6-PD deficiency, hereditary spherocytosis and the like. In these disorders, a greatly shortened red cell life span results in continuous large depositions of iron in tissues to an extent exceeding the capacity of the body to re-utilize the metal. Thus tissue concentrations of iron rise to very high, toxic levels and lead to impairment of vital organ functions manifest for example by cardiomyopathy, pancreatic insufficiency (diabetes) and generalized endocrine failure.

A principal cause of abnormal iron is the iron in foodstuffs, particularly those of animal origin. This invention is particularly useful in neutralizing this potential source of excessive iron.

There is no physiological mechanism for excreting this excess of iron and the only generally available therapeutic modality for this purpose is a pharmacological agent known as desferrioxamine. This agent is not specific for iron however and chelates other metals as well; it must in order to be reasonably effective be given intramuscularly and causes substantial local inflammation at the site of injection. Further, original suggestions that it was non-toxic have proved incorrect and a large number of toxic reactions in treated patients have now been reported to occur after its use, including hypotension and allergic reactions.

For animals suffering from a chronic excess of iron, regardless of the source of this condition, it is desirable to have available methods and materials to inhibit the catabolism of heme from foodstuffs in the small intestine so that the absorption of iron compounds from foodstuffs is prevented. In particular, an oral composition for preventing the catabolism by intestinal heme oxygenase of heme from foodstuffs and the concommitant absorption of iron compounds from said foodstuffs is needed, especially or individuals suffering from a chronic excess of iron, regardless of the source of this condition.

Sn-protoporphyrin (SnPP) as described in copending and commonly assigned U.S. patent application Ser. No. 07/325,086, filed Mar. 16, 1989, manifests the extremely advantageous property of greatly enhancing the biliary excretion of iron into the intestinal contents where the metal is eliminated. Sn-PP is administered parenterally and acts in this additional fashion by blocking the binding of heme to heme oxygenase, thus preventing the release of iron which normally occurs in the process of heme catabolism and allowing one atom of iron to be excreted into the intestine with every molecule of uncatabolized heme.

In commonly assigned U.S. Pat. No. 4,657,902, Sn-mesoporphyrin (Sn-MP) is employed parenterally in the treatment of mammals, including humans, in need of such treatment, to increase the rate at which heme is excreted, to decrease the rate of heme metabolism, and to control the rate of tryptophan metabolism in the liver.

Commonly assigned U.S. Pat. No. 4,619,923 concerns a method of increasing the rate of tryptophan metabolism in the liver of humans in need of such increase through the parenteral administration of an effective amount of tin. In addition, commonly assigned U.S. Pat. No. 4,782,049 relates to the parenteral administration of SnPP and SnMP together with ultraviolet light in the treatment of psoriasis.

Commonly assigned U.S. Pat. No. 4,684,637 relates to preventing hyperbilirubinemia in mammals by decreasing the rate of heme metabolism through parenteral administration of tin protoporphyrin and chromium protoporphyrin.

All of these patents refer to parenteral administration. So far as is known, there has not, heretofore, been any teaching or suggestion of administering these products orally for any purpose. Heretofore there has been no proposal to employ metalloporphyrins or oral compositions containing these compounds for inhibiting the activity of intestinal heme oxygenase and thereby reducing the absorption of iron from foodstuffs by animals in need of such prevention. Moreover, heretofore it was believed that there is no inhibition of intestinal heme oxygenase either in vitro or in vivo after administration of SnPP (See Hintz et al, Ped. Res. 23: 50–53 (1988)).

SUMMARY OF INVENTION

It has now been discovered that certain metalloporphyrins can be administered to animals orally for inhibiting intestinal heme oxygenase activity in the small intestine and thereby reducing the absorption of iron from foodstuffs. The metalloporphyrins particularly useful in the practice of this invention include tin protoporphyrin (SnPP), tin mesoporphyrin (SnMP), chromium protoporphyrin, CrPP and chromium mesoporphyrin (CrMP).

Accordingly, the present invention provides compositions for oral administration to inhibit the absorption of iron in animals in need of such inhibition, comprising an effective amount of tin protoporphyrin, tin mesoporphyrin, chromium protoporphyrin, chromium mesoporphyrin, or mixtures thereof. The tin compounds are particularly preferred.

The present invention also provides a method for reducing the catabolism of heme in the small intestine and the concomitant absorption of iron by orally administering an effective amount of tin protoporphyrin, tin mesoporphyrin, chromium protoporphyrin, chromium mesoporphyrin.

Presently preferred embodiments within the scope of the invention will be apparent from the following detailed description.

DETAILED DESCRIPTION

Figure 1:
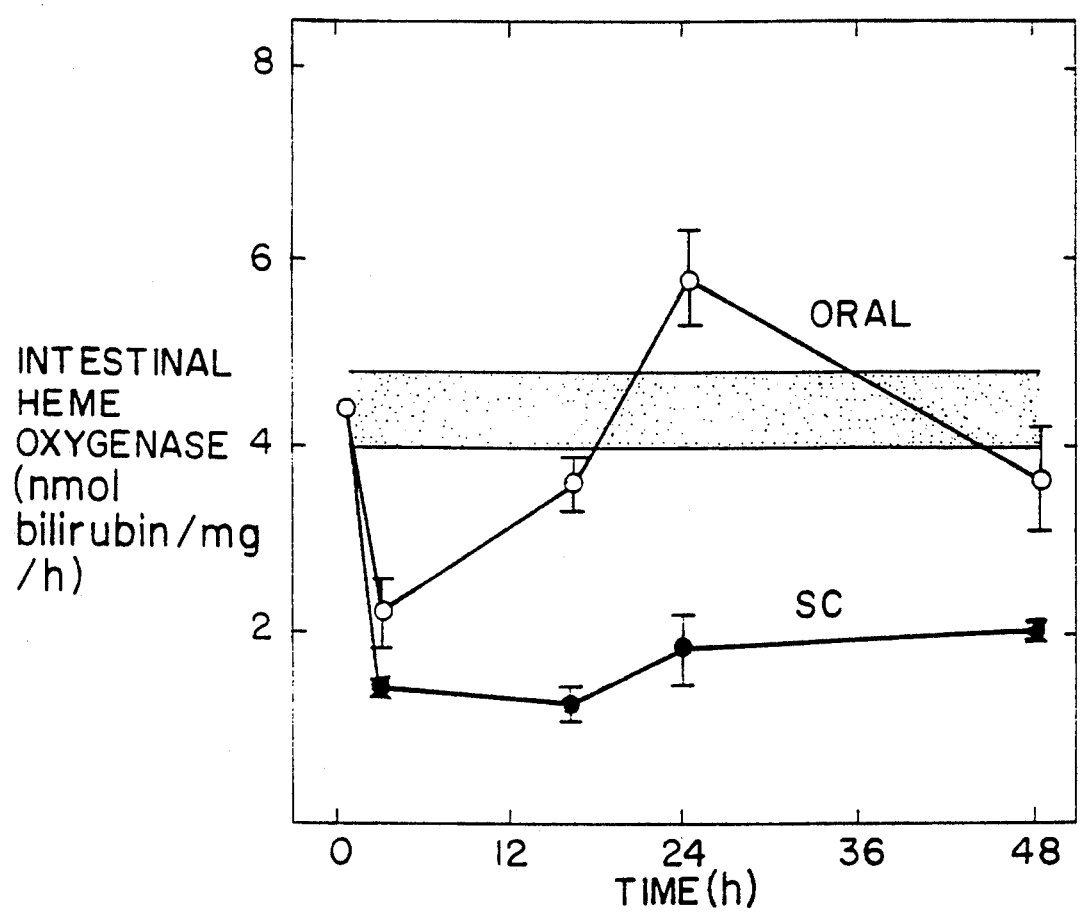
FIG. 1 illustrates the effect of SnPP on intestinal microsomal heme oxygenase activity. SnPP was administered in a single dose (25 umoles/kg body weight) either orally (o) or parenterally (o) and heme oxygenase activity determined. Each point represents the mean±SE of four individual animals. Similar results obtain for other metalloporphyrins with the scope of the present invention.

Heme oxygenase is the rate-limiting enzyme in the catabolism of heme (e.g., in the liver,) to bile pigments and iron compounds. Heme oxygenase activity in the small intestinal epithelium has now been found to be comparable to that of the liver. Furthermore, intestinal heme oxygenase has a physiological role in iron absorption because of its role in the regulation of the amount of inorganic iron that is released from heme and sources of heme, e.g., foodstuffs containing heme.

Thus, by regulating the activity of intestinal heme oxygenase, one can also regulate the absorption of iron from heme and sources of heme, e.g., foodstuffs containing heme. Such regulation of the activity of intestinal heme oxygenase is quite useful in treating animals suffering from a chronic excess of iron, regardless of the source of this condition.

It has now been discovered that certain synthetic metalloporphyrins produce a pronounced inhibition of intestinal microsomal heme oxygenase when administered orally. Further, synthetic metalloporphyrins so administered act as a competitive inhibitor of heme oxygenase, with a $K_i$ (rate of inhibition) similar to that for heme oxygenase isolated from the liver and spleen.

The present invention is demonstrated by the following non-limiting examples.

MATERIALS AND METHODS

Male Sprague-Dawley rats (175–225 g) were purchased from Taconic Farms (Germantown, NY). SnPP (synthetic heme analogue) was purchased from Porphyrin Products (Logan, UT). Ultrex grade nitric acid (J. T. Baker Chemical Co., Phillipsburg, Pa.) was used for sample digestions and preparation of standards for tin analysis. All other reagents were of the highest grade commercially available and were purchased from Sigma Chemical Co. (St. Louis, Mo.).

Treatment of animals

Rats were maintained on Standard Purina Rodent Chow (St. Louis, Mo.), and were allowed to acclimatize to a light-cycled room (12 hr light/dark cycle) for at least one week prior to study. SnPP was dissolved in a small volume (0.2 ml/ml final volume) of 0.2N $Na_3PO_4 12H_2O$, adjusted to pH 7.4 with 1M HCl and made up to a final volume with 0.9% NaCl under subdued light. SnPP was administered either subcutaneously or by gavage in a single dose of 25 umoles/kg body weight (4.0 ml/kg body weight). Control rats received an equivalent volume of diluent. All rats were allowed free access to food and water.

Preparation of subcellular fractions and enzyme assays

Animals were sacrificed at the times indicated in the legend to the Table and in the above and following descriptions of the Figures, and then exhaustively perfused in situ with ice-cold 0.9% NaCl through the left ventricle. The small intestine was cut at the pyloric junction and the entire length of the intestine irrigated in situ with 30 ml of ice-cold 0.9% NaCl to remove intestinal contents. Beginning at 5 cm, a 20 cm segment of small intestine was excised and irrigated once more with 30 ml of saline. The mucosa was then gently scraped off with a stainless steel scalpel and placed in ice-cold potassium phosphate buffer (0.1M, pH 7.4), containing sucrose (0.25M), 20% glycerin (v/v), trypsin inhibitor (5 mg/ml), and heparin (3 U/ml), as described by Stohs et al, Arch. Biochem Biophys. 177: 105–116 (1976). Following sonication and homogenization, intestinal microsomes were then prepared by differential centrifugation as described in Rosenberg et al, Biochem. Pharmacol. 38: 1155–1161 (1988). The microsomal pellet was rinsed and resuspended in 1.5 ml of potassium phosphate buffer (0.1M, pH 7.4) to a protein concentration of approximately 5–10 mg/ml. Microsomes were freshly prepared on a daily basis for all subsequent assays. The activity of heme oxygenase was determined as described in Maines et al, J. Biol. Chem. 250: 4171–4178 (1975), using the 105,000xg supernatant fraction derived from normal rat liver as the source of biliverdin reductase, and a hemin concentration of 50 uM. Bilirubin formation was calculated using an absorption coefficient of 40 $mm^1 cm^1$ between 464 and 530 nm (See Maines et al, Proc. Natl. Acad. Sci. USA 71: 4293–4297 (1974)). Protein content was determined by method of Lowry et al, J. Biol. Chem. 193: 265–275 (1951) suing bovine serum albumin as a standard.

Tin analysis

All tin analyses were performed on Zeeman/5000 atomic absorption spectrophotometer equipped with an HGA-500 graphite furnace Perkin-Elmer Corp., Norwalk, Conn.). The graphite furnace utilized the L'vov platform (See Slavin et al, At. Spectrosc. 2: 137-145 (1981)) with an appropriate wavelength (286.4 nm) and instrumental operating conditions as recommended by the manufacturer and optimized in our laboratory for tin measurement. All tin analyses included magnesium nitrate and ammonium phosphate in 20% nitric acid as a matrix modified.

Results

A single does of SnPP (25 umoles/kg b.w.) was administered either orally or parenterally to rats, and heme oxygenase levels were determined in the small intestinal epithelium at the times indicated in FIG. 1. This dose was selected to match that previously used by other investigators (See Hintz et al, Ped. Res. 23: 50-53 (1988)). Following oral treatment, heme oxygenase activity was rapidly (within 3 hours) inhibited (50% of controls), but the levels returned to normal within 16-24 hours after treatment. Following parenteral treatment, enzyme activity was inhibited to an even greater extent (65% inhibition), and these markedly decreased levels of enzyme activity persisted for at least 48 hours after a single dose of metalloporphyrin.

A similar experiment was conducted utilizing CrMP. The results are shown in Table I.

TABLE I

Heme Oxygenase Activity in the Gut after Oral Administration of 25 umol/Kg CrMP

|  | Average | P value* |
|---|---|---|
| Control | 2.70 + 0.09 |  |
| 3 hours | 0.64 + 0.38 | $p < 0.01$ |
| 16 hours | 1.04 + 0.02 | $p < 0.001$ |
| 24 hours | 1.85 + 0.07 | $p < 0.001$ |
| 48 hours | 2.57 + 0.07 |  |

*Student's t test

Figure 2:
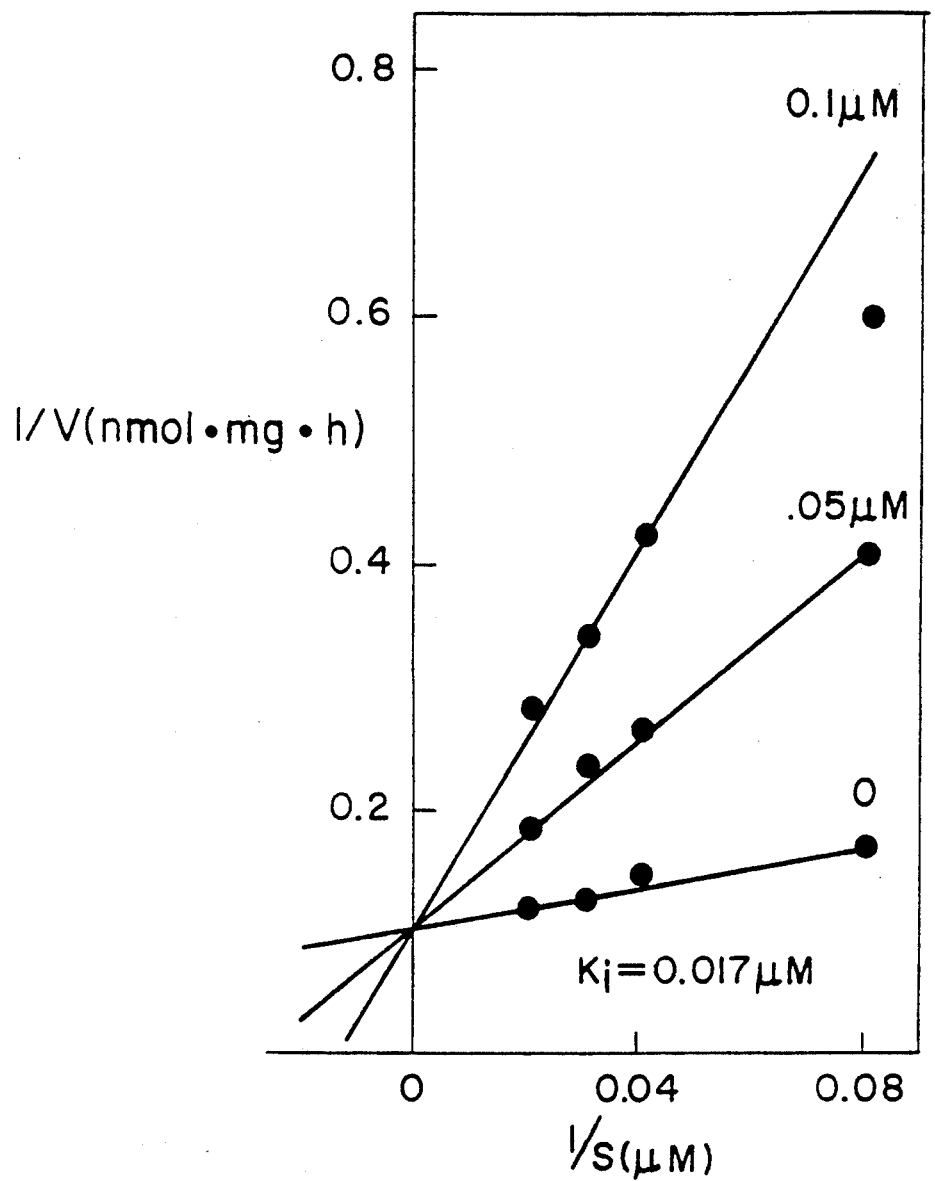
FIG. 2 illustrates the competitive inhibition of intestinal microsomal heme oxygenase in vitro by SnPP. SnPP (o) was added to intestinal microsomes at concentrations of 0, 0.05 uM. The heme concentration was 50 uM. Heme oxygenase activity was determined as described below under Materials and Methods. Each point represents the mean of at least 3 individual experiments. Similar results obtain for other metalloporphyrins within the scope of the present invention.

As shown in FIG. 2, the apparent Km for the substrate, heme, in intestinal microsomes was determined by linear regression analysis to be 8.21 uM. This is similar to the Km reported for heme in hepatic and splenic microsomes (See Kappas et al, J. Clin. Invest. 77: 335-339 (1986); Yoshinaga et al, J. Biol. Chem. 257: 7778-7785 (1982)). The addition of SnPP (0.05 and 0.1uM) to intestinal heme oxygenase incubation mixtures surprisingly resulted in a marked competitive inhibition of enzyme activity, with a 3- to 7-fold increase in the Km for heme (23.92 and 56.18 uM, respectively). The Ki for SnPP in intestinal microsomes was determined to be 0.017 uM.

Tissue tin levels (ug/gm dry wt.) were determined in the liver, kidney and spleen 48 hours after a single dose (25 umoles/kg b.w.) of SnPP. As shown below in Table II, tin accumulated to a similar extent in the liver and kidney after a single parenteral dose of metalloporphyrin (14.43 +1.50 and 14.39 +0.45 ug/gm, respectively), considerably less tin was found in the spleen at this time point (1.78+0.03 ug/gm). After oral treatment, however the liver and kidney accumulated no more than 1.5 and 3.5%, respectively, as much tin as was found in these organs after parenteral treatment. These levels of tissue tine indicate a very low degree of absorption to the compound from the gastrointestinal tract, a finding consistent with that reported previously in humans (See Anderson et al, Clin. Pharm. Therapeut. 39: 510-520 (1986)).

TABLE II

The effects of oral and parenteral administration of SnPP on tissue tin levels at 48 hours

| Tissue | Parenteral Tin (um/gm dry weight) | Oral |
|---|---|---|
| Liver | 14.34 + 1.50 | 0.50 + 0.11 |
| Kidney | 14.39 + 0.45 | 0.14 + 0.02 |
| Spleen | 1.78 + 0.03 | 0.32 + 0.05 |

For Table II: SnPP was adminsitered to rats in a single dose (25 umoles/kg body weight) either orally or subcutaneously. Tissue tin levels were determined 48 hours later by graphite furnace atomic absorption spectroscopy. Values reported as the means±SE of four individual animals as described above in Materials and Methods. The tissue levels of tin in the control animals were below detection levels. These examples demonstrate the potent ability of heme analogue, metalloporphyrins especially SnPP, SnMP, CrPP, CrMP, and mixtures thereof, to inhibit microsomal heme oxygenase in the epithelium of the small intestine, especially at the site of heme-derived iron absorption provides novel material sand methods for inhibiting iron absorption and thus extends the biological actions of these compounds to a tissue that is critical both to "first-pass" cytochrome P-450-dependent drug metabolism and the regulation of nutrient uptake, including iron derived from heme from dietary sources. The proximal region of the small intestine contains high levels of heme oxygenase activity (See Raffin et al, J. Clin. Invest. 54: 1344-1352 (1974). In addition, this region of the gut is the most active site for hemoglobin-iron uptake, a process that requires heme oxygenase (Id.) Thus, pharmacological inhibition of heme oxygenase in the gut has considerable experimental usefulness as well as clinical applications, especially in the treatment of animals, including humans afflicted with a chronic excess of iron, regardless of the source of this condition.

In administering the metalloporphyrins of the present invention, the physician or veterinarian in attendance will consider the age and weight of the human or animal being treated, the type and severity of the condition being treated, and other factors readily evaluated.

The metalloporphyrins of the present invention may be administered orally in pure solid form, in dilute solutions or suspensions or in concentrates and prepared for unit dose or multi-dose administration.

In respect to pharmaceutical compositions containing the metalloporphyrins of the present invention, carrier and other ingredients should be such as to not diminish the therapeutic effects or the metalloporphyrins. Suitable dosage forms for oral use are tablets, dispersible powders, granules, capsules, caplets, gum tragacanth, suspensions, syrups, elixirs, and the like. For ease of administration, liquid compositions are preferred dosage forms. Capsules can contain the metalloporphyrins of the present invention in either a solid form or a liquid form.

The pharmaceutical compositions containing the metalloporphyrins of the present invention may contain one or more conventional adjuvants, such as sweetening agents, flavoring agents, coloring agents and preserving agents, in order to provide suitable pharmaceutical compositions. Solid dosage forms containing the metalloporphyrins of the present invention, (e.g., tablets, capsules, caplets, and the like, may contain the active ingredient (i.e., the metalloporphyrin) in admixture with conventional acceptable excipients including inert diluents such as calcium carbonate, sodium carbonate, calcium phosphate, lactose, talc, Kaolin and the like; granulating and disintegrating agents such as starch, alginic acid, and the like; binding agents such as starch, gelatin, acacia and the like; and lubricating agents such as magnesium stearate, stearic acid, talc, and the like. Such solid dosage forms may be uncoated or coated by known techniques to delay the effect of the active ingredient and provide sustained action.

Similarly, suspensions, syrups, elixirs, and the like may contain the active ingredient in admixture with any of the conventional excipients utilized for the preparation of such compositions such as suspending agents (e.g., methylcellulose, tragacanther, and sodium alginate), wetting agents, (e.g., lecithin, polyoxyethylene stearate) and preservatives.

The daily dosage of the active ingredient for adult animal, including human treatment will preferably range from about 0.1 to 50 uM/kg body weight in single or multiple doses. The dosage unit of the active ingredient in pharmaceutical compositions for administration to adult animals, including humans, will preferably range from about 0.07 to 40.0 mg/g. Depending on the nature and severity of the condition being treated, and the size and mass of the patient (70 kg taken as average for adult human), e.g., the treatment of neonates, infants and juveniles, smaller dosages than adult dosages may be effected. Likewise, the active ingredient may be administered in a single dosage or in multiple dosages, e.g., a dosage every 12 hours.

Appreciable variations from these ranges are possible without adverse effect. The pharmencetical compositions of the present invention thus will generally comprise oral compositions containing an effective amount of SnPP, SnMP, CrPP, CrMP, or mixtures thereof, preferably SnPP or SnMP, (i.e., an amount effective usefully to inhibit the activity of intestinal heme oxygenase and prevent the absorption of iron from heme and sources of heme such as foodstuffs); said oral compositions can include pharmaceutically acceptable carriers such as water, alcohols or the like, fillers, stabilizers, and wetting agents to name but a few conventional carriers, adjuvants and excipients which may be employed.

Apparent variations of the present invention which are possible without departing from the spirit and scope thereof are included within the present invention.

What is claimed is:

1. A pharmaceutical composition for oral administration useful to inhibit heme oxygenase activity in the intestine thereby to inhibit absorption of iron in animals in need of such inhibition comprising a pharmaceutically acceptable oral carrier together with an amount of tin mesoporphyrin useful to effect such inhibition.

2. A pharmaceutically composition for oral administration useful to inhibit heme oxygenase activity in the intestine thereby to inhibit absorption of iron in animals in need of such inhibition comprising a pharmaceutically acceptable oral carrier together with an amount of chromium mesoporphyrin useful to effect such inhibition.

3. A method for inhibiting heme oxygenase activity in the intestine thereby to inhibit intestinal absorption of iron in animals in need of such inhibition by orally administering an amount of tin protoporphyrin, tin mesoporphyrin, chromium protoporphyrin, chromium mesoporphyrin, or mixtures thereof which is effective to effect such inhibition.

4. A method as claimed in claim 3 wherein the animal is a mammal.

5. A method as claimed in claim 4 wherein the animal is a human.

6. A method as claimed in claim 5 wherein the effective amount is adminsitered in dosage unit form.

7. A method as claimed in claim 6 wherein each a dosage unit contains from, about 0.07 to 40.0 mg/g.

8. A method as claimed in claims 3, 4, 5, 6, or 7 wherein the compound is tin protoporphyrin.

9. A method as claimed in claims 3, 4, 5, 6, or 7 wherein the compound is tin mesoporphyrin.

* * * * *